United States Patent

Carls et al.

[11] Patent Number: 5,693,056
[45] Date of Patent: Dec. 2, 1997

[54] ORTHOPAEDIC SURGICAL CUTTING BLOCK AND SAW CAPTURE APPARATUS

[75] Inventors: Thomas A. Carls, Memphis; Steven M. Tammi, Collierville, both of Tenn.

[73] Assignee: Smith & Nephew, Inc., Memphis, Tenn.

[21] Appl. No.: 603,398

[22] Filed: Feb. 20, 1996

[51] Int. Cl.⁶ .................................................. A61B 17/15
[52] U.S. Cl. .................. 606/86; 606/87; 606/82; 606/88; 606/96
[58] Field of Search .................. 606/82, 86–89, 606/96, 102

[56] References Cited

U.S. PATENT DOCUMENTS

| | | |
|---|---|---|
| 4,474,177 | 10/1984 | Whiteside . |
| 4,487,203 | 12/1984 | Androphy . |
| 4,703,751 | 11/1987 | Pohl . |
| 4,722,330 | 2/1988 | Russell et al. . |
| 4,892,093 | 1/1990 | Zarnowski et al. ............... 606/82 |
| 4,935,023 | 6/1990 | Whiteside et al. ............... 606/88 |
| 5,415,663 | 5/1995 | Luckman et al. ............... 606/86 |

OTHER PUBLICATIONS

Smith & Nephew Genesis™ Total Knee System Catalog.

*Primary Examiner*—Michael Buiz
*Assistant Examiner*—Daphna Shai
*Attorney, Agent, or Firm*—Pravel, Hewitt, Kimball & Krieger

[57] ABSTRACT

A surgical instrument for shaping a patient's bone tissue at the joint to receive an implant includes a cutting block body that is sized and shaped to fit a patient's long bone at the joint during joint replacement surgery. The block is attachable to the patient's bone tissue at the joint area. A flat cutting guide surface on the block body is provided for guiding a surgeon's saw blade when the surgeon cuts bone tissue at the joint. A saw capture removably attaches to the block body at or near the flat cutting guide surface. The saw capture also provides a flat cutting guide surface thereon that is positioned generally parallel to the cutting guide surface on the block body during use, a gap being formed therebetween. Wedge locking connections are provided for affixing the saw capture to the block body at the flat cutting guide surface. The connection includes first and second interlocking connecting portions that are respectively on the block body and saw capture. The saw capture is gradually wedged against the block body upon assembly of the block body and the saw capture so that the flat cutting guide surface of the saw capture and the flat cutting guide surface of the block body gradually approach one another upon such assembly.

18 Claims, 3 Drawing Sheets

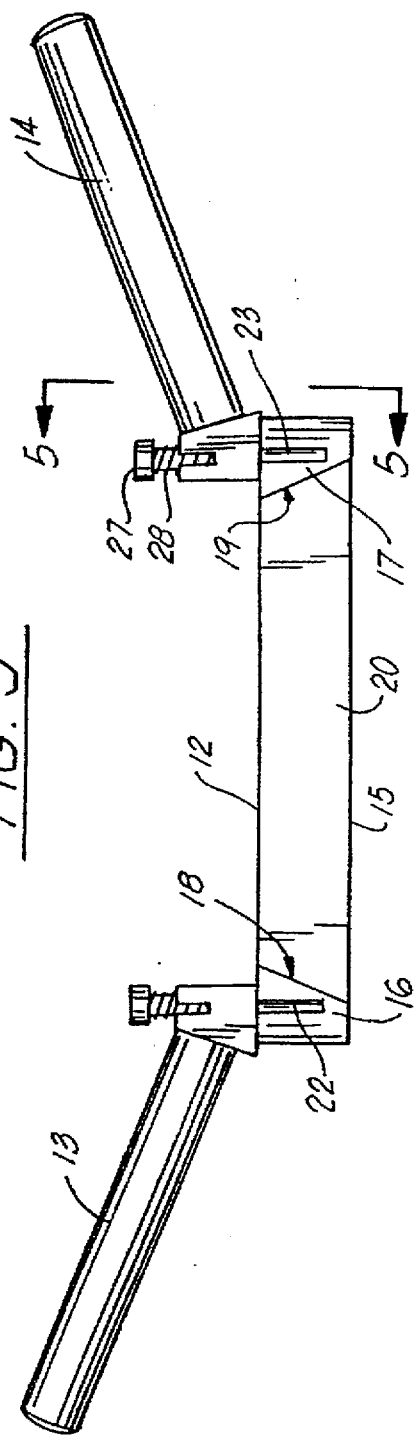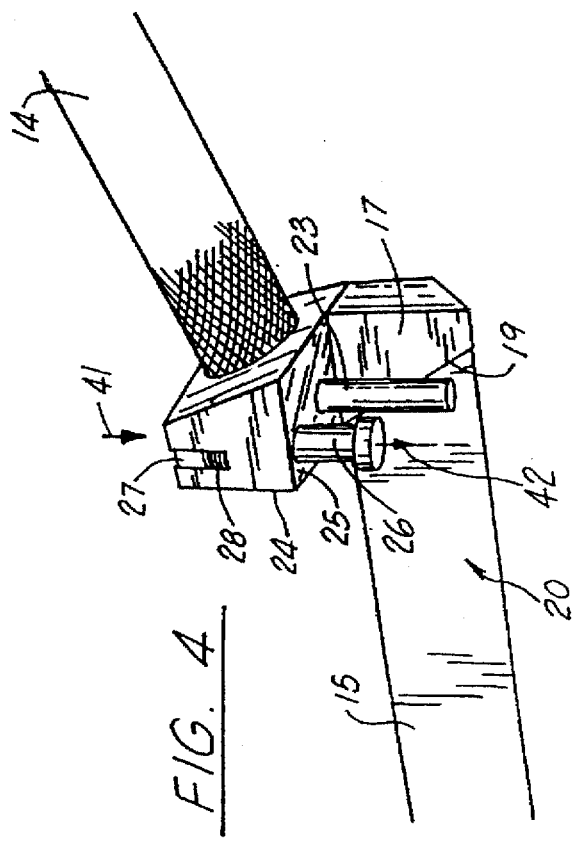

ORTHOPAEDIC SURGICAL CUTTING BLOCK AND SAW CAPTURE APPARATUS

BACKGROUND OF THE INVENTION

1. Field of the Invention

The present invention relates to surgical instruments such as those that can be used for shaping a patient's bone tissue at a joint area (e.g., knee joint). More particularly, the present invention relates to an improved cutting block and surgical saw capture apparatus wherein the saw capture removably attaches to a cutting block body at or near a flat cutting guide surface and wherein the saw capture has a corresponding flat guide surface that is positioned generally parallel to the cutting guide surface of the block body. Even more particularly, the present invention relates to an improved orthopaedic surgical cutting saw apparatus wherein a wedging action wedges two corresponding saw cutting guide surfaces toward each other during an affixation of the saw capture to the cutting block.

2. General Background

During the surgical preparation of bone tissue such as a patient's knee or shoulder joint, cutting instruments are used to prepare the bone to receive a prosthesis. Cutting guide instruments are known that provide permanent slots through which the surgeon passes a saw blade of the type used to cut the bone tissue. Slots on the cutting instrument track the saw along a desired path.

Some surgical orthopaedic cutting blocks have a saw capture that is attached to the cutting block in order to provide a second guide surface spaced from the cutting block. This holds or captures the saw blade used to cut the bone tissue thus enabling the surgeon to cut while the saw occupies a plane. Some commercially available cutting blocks have a removable saw capture that attaches to the block using pegs or pins.

One of the problems with presently available cutting blocks that have removable saw captures is that the saw capture can move slightly during the cutting operation. Movement of the saw capture relative to the block causes the saw blade to wander from its intended planar path. This can create surgical cuts that are imprecise. Imprecise cuts create a poor fit between the surgically prepared bone tissue and the prosthesis to be implanted.

Several knee cutting instruments have been patented that relate to cutting blocks that are used to prepare bone tissue. The Whiteside U.S. Pat. No. 4,474,177 provides a method and apparatus for preparing the distal surface of the femur to receive a distal femoral prosthesis employing an intramedullary reamer that is used to internally locate the central longitudinal axis of the femur and an intramedullary alignment guide which is inserted into the space in the intramedullary canal upon removal of the reamer and at least one femoral surface modifying instrument which cooperatively engages with a guide handle attached to the intramedullary alignment guide to accomplish the shaping of the distal femoral surface.

U.S. Pat. No. 4,487,203 discloses a resection system for preparing a knee. The apparatus discloses a set of instruments that include femur and tibia guide rods, a tibia adapter, a tibia bar, and a femur bar for establishing equal flexion and extension gaps and triplanar resections.

U.S. Pat. No. 4,703,751 discloses another cutting instrument that has blade guides thereon. U.S. Pat. No. 4,722,330 discloses a device for shaping the femur using a shaping guide.

U.S. Pat. No. 4,892,093 issued to Zarnowski et al. discloses a cutting guide for guiding a saw blade during the preparation of a femur to receive a femoral component of a knee prosthesis. Guide surfaces on the cutting instrument enable the cutting of multiple cuts including anterior, posterior, and chamfer cuts.

The Whiteside U.S. Pat. No. 4,935,023 relates to a distal femoral surface shaping guide for mounting on an intramedullary alignment rod which references the central long axis of the femur. The apparatus has applicability for shaping one condyle for attachment of a unicondylar prosthesis.

Some commercially available saw capture devices include, for example, the Intermedics Natural Knee System and Smith & Nephew Richards Genesis Total Knee System.

SUMMARY OF THE INVENTION

The present invention provides an improved surgical instrument for shaping a patient's bone tissue at the knee joint to receive an implant.

The apparatus includes a cutting block body that is sized and shaped to fit a patient's long bone at the joint area such as a femur or tibia during knee joint replacement surgery. The block is attachable to the patient's bone tissue at the knee joint area or like joint.

A flat cutting guide surface on the block body is provided for guiding a surgeon's saw blade when the surgeon cuts bone tissue at the knee joint.

A saw capture removably attaches to the block body at or near the flat cutting guide surface, the saw capture having a corresponding flat guide surface thereon that is positioned generally parallel to the cutting guide surface of the block body during use.

A wedge locking connection is provided for affixing the saw capture to the block body so that the flat cutting guide surfaces of the block body and saw capture are rigidly positioned and parallel relative to one another. The connection includes first and second interlocking connecting portions that are respectively on the block body and the saw capture.

The saw capture is gradually wedged against the block body upon assembly of the block body and saw capture so that the flat cutting guide surface of the saw capture and the flat cutting guide surface of the block body gradually approach one another upon assembly.

The cutting block body can include flat surfaces for preparing patient's distal femur to receive anterior and posterior cuts.

The cutting block body can include diagonally extending flat cutting guide surfaces that enable a surgeon to prepare anterior and posterior chamfer cuts on a patient's distal femur. The same saw capture can be removably affixed to a number of different surgical instruments.

The cutting block body can be a composite cutting block that includes a plurality of flat cutting guide surfaces thereon including at least a flat cutting guide surface that enables a surgeon to make anterior and posterior cuts on a patient's distal femur and also diagonally extending cutting guide surfaces that enable a surgeon to make chamfer cuts.

A gap is provided between the saw capture flat cutting guide surface and the flat cutting guide surface of the block body. The gap is sized and shaped to allow a surgeon's saw to barely fit through the slot. Thus, the saw capture and cutting block body guide surfaces closely conform to the surfaces of the saw during a cutting of the patient's bone tissue.

The wedge locking connection of the present invention includes connecting members on the end portions of the saw capture that form a connection with cooperating connecting portions on the block body, so that the gap is defined as the distance between the saw capture and the block body guide surfaces and its length is defined in between the end connecting portions.

The wedge locking connection can include spaced upon sockets on the block body and cooperating spaced apart pins on the saw capture that fit the sockets.

Spaced apart bearing or engagement surfaces can be provided on the saw capture that engage the block body upon assembly, wherein the bearing surfaces are forced tightly against the block body upon assembly but the gap is formed at the central part of the saw capture spaced away from the bearing surfaces.

The wedge locking connection can include cooperating sockets and pins respectively on the block body and saw capture, the sockets being angled with respect to the flat cutting guide surfaces of the saw capture and block body.

With the present invention, tight tolerances for gap thickness can be held. For example, the gap thickness can be held to a desired dimension within ±0.001 inches as a tolerance.

BRIEF DESCRIPTION OF THE DRAWINGS

For a further understanding of the nature and objects of the present invention, reference should be had to the following detailed description, taken in conjunction with the accompanying drawings, in which like parts are given like reference numerals, and wherein:

FIG. 3 is a frontal view of the saw capture portion of the preferred embodiment of the apparatus of the present invention;

FIG. 4 is a partial perspective view of the saw capture portion of the preferred embodiment of the apparatus of the present invention;

FIG. 5 is a sectional view taken along lines 5—5 of FIG. 3;

DETAILED DESCRIPTION OF THE PREFERRED EMBODIMENT

Figure 2:
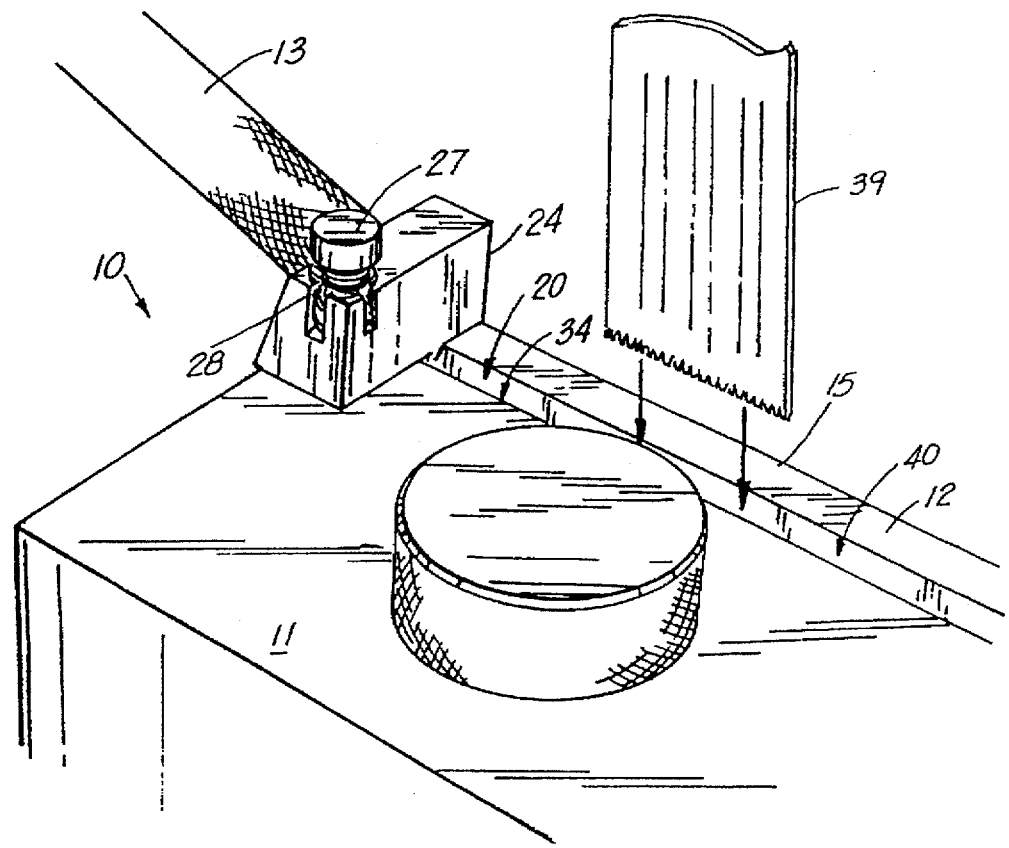
FIG. 2 is a partial perspective view of the preferred embodiment of the apparatus of the present invention.
Figure 1:
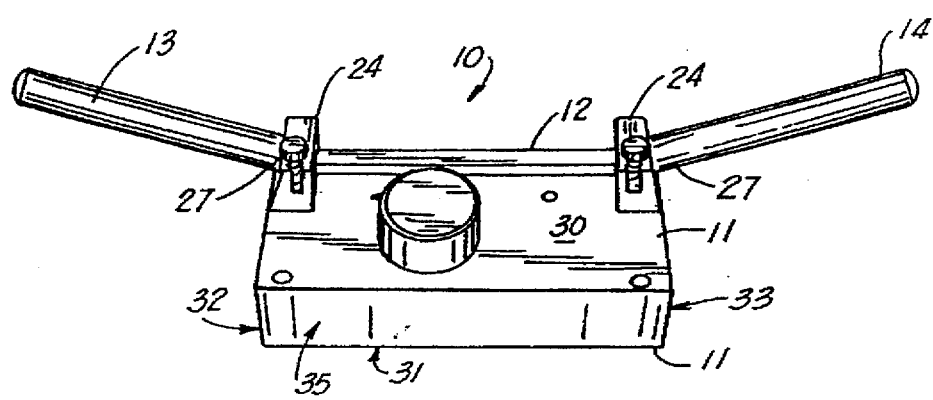
FIG. 1 is a perspective view of the preferred embodiment of the apparatus of the present invention.

FIGS. 1 and 2 show generally the preferred embodiment of the apparatus of the present invention designated generally by the numeral 10. Cutting instrument 10 includes a block body 11 to which a removable saw capture 12 can be attached for forming a gap 40 through which a surgeon's cutting saw 39 can be guided and directed during a surgical cutting of adjacent bone tissue. The gap 40 is only slightly thicker than the thickness of the saw blade so that the saw blade is maintained in a plane during cutting.

Saw capture 12 has a pair of spaced apart handles 13, 14 that aid in manipulating the saw capture 12 during assembly.

Further, once saw capture 12 and block body 11 are attached together, the handles 13, 14 can be used to manipulate the assembly. A bar 15 extends between a pair of connector portions 24. The bar 15 includes end portions 16, 17 in the form of raised bearing surfaces that engage a flat cutting guide surface 34 of cutting block 11 during use. Shoulders 18, 19 interface between raised bearing surfaces 16, 17 and flat cutting guide surface 20 of saw capture 12.

The flat saw guide surface 20 of saw capture 12 and the flat guide surface 34 of cutting block 11 form a gap 40 that has a thickness equal to the thickness of the shoulders 18, 19. Saw capture 12 has second flat surface 21 that is opposite flat saw guide surface 20.

The saw capture 12 has a pair of cylindrically-shaped pins 22, 23 that extend along a line that is generally parallel to the surfaces 16, 17 and 20. Each connector 24 carries a pushrod 26 that slides in an opening 29 with respect to the saw capture 12. Each pushrod 26 can be moved downwardly in the direction of arrows 41, 42 by pushing on actuator button 27 to overcome spring 28.

Figure 6:
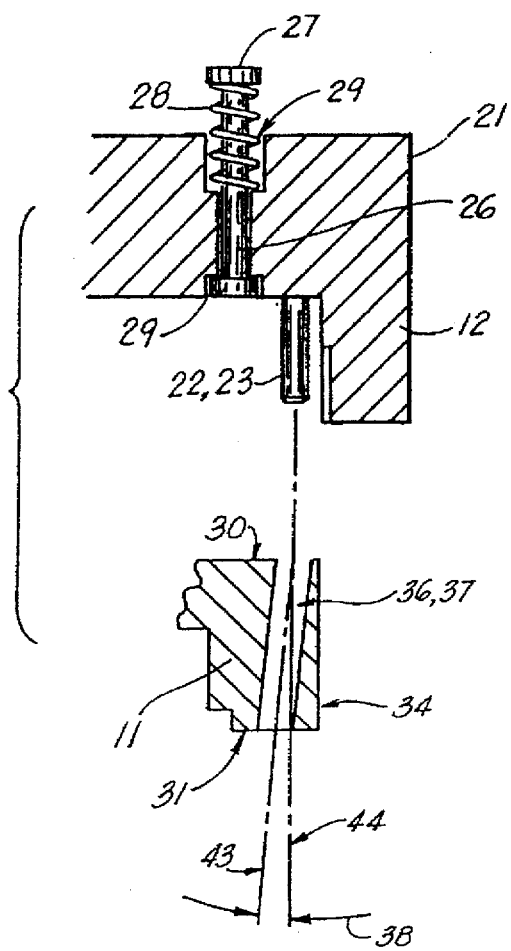
FIG. 6 is a partial sectional view of the preferred embodiment of the apparatus of the present invention shown prior to an assembly of the saw capture to the block body.

When the user releases the actuator button 27, the spring 28 returns the push button 27 and pushrod 26 to an upper position as shown in FIGS. 3 and 6. When the user pushes the button 27 downwardly, the pushrod 26 moves in the direction of arrows 41, 42 in order to disengage saw capture 12 from block 11. Opening 29 through each connector 24 houses a pushrod 26, its spring 28, and the actuator button 27.

As shown in FIGS. 1, 2, and 7–8, cutting block body 11 has a number of flat surfaces, some of which can be parallel if desired. Proximal surface 30 and distal surface 31 are flat preferably parallel surfaces. The anterior and posterior sides 34, 35 of cutting block 11 are flat and can be generally parallel. The sides 32, 33 can be parallel if desired as shown in FIG. 1.

Figure 7:
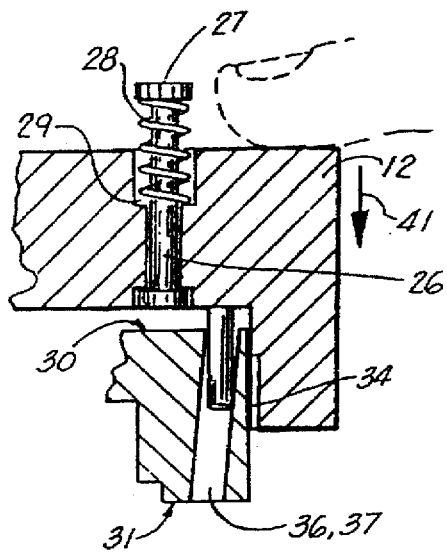
FIG. 7 is a partial sectional view of the preferred embodiment of the apparatus of the present invention after an assembly of the saw capture to the block body.
Figure 8:
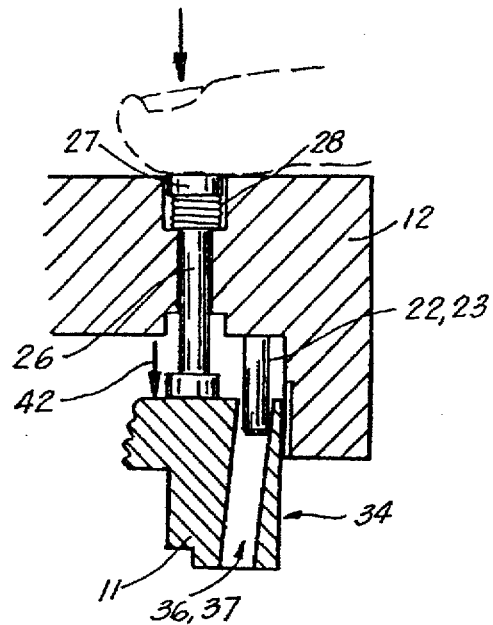
FIG. 8 is a partial sectional view illustrating a disassembly of the saw capture and block body.

FIGS. 6–8 illustrate the attachment of saw capture 12 to cutting block body 11. In FIG. 6, the cutting block 11 is shown as including one or more angled openings 36, 37. In the embodiment of FIGS. 1–8, a pair of spaced apart openings 36, 37 are provided, one for each connector 24 as shown in FIG. 1.

Each pin 22, 23 registers respectively in an angled opening 36, 37 of block 11. The angle 38 in FIG. 6 shows that openings 36, 37 have a central axis 43 that forms an angle with the axis 44 of the connector pins 22, 23. The line 44 is parallel to surface 34 of block 11. In FIG. 7, the pins 22, 23 have been forced downwardly into the angled openings 36, 37. This causes a wedging action between the saw capture 12 and block 11. As the saw capture 12 is moved downwardly, the pins 22, 23 are wedged so that the surfaces 16, 17 are forced closer and closer to the surface 34 and more tightly into engagement therewith.

This wedging action ensures that a very tight connection will be made between the surfaces 16, 17 of saw capture 12 and the flat cutting guide surface 34 of block 11. Because the surfaces 16, 17 are raised surfaces relative to the cutting guide surface 20 of saw capture 12, a gap will be provided in between the flat surface 20 of saw capture 12 and the flat surface 34 of cutting block 11. This gap 40 as shown in FIG. 2 extends between the shoulders 18, 19.

In FIG. 8, a disassembly of the block 11 and saw capture 12 is illustrated. The user presses upon the button 27 so that the pushrod 26 moves down to engage the upper surface 30 of block 11 thus disengaging the pins 22, 23 from the angled openings 36, 37.

The following table lists the parts numbers and parts descriptions as used herein and in the drawings attached hereto.

PARTS LIST

| Part Number | Description |
| --- | --- |
| 10 | knee cutting instrument |
| 11 | block body |
| 12 | saw capture |
| 13 | handle |
| 14 | handle |
| 15 | bar |
| 16 | raised bearing surface |
| 17 | raised bearing surface |
| 18 | shoulder |
| 19 | shoulder |
| 20 | flat saw guide surface |
| 21 | flat surface |
| 22 | pin |
| 23 | pin |
| 24 | connector |
| 25 | undersurface |
| 26 | pushrod |
| 27 | actuator button |
| 28 | spring |
| 29 | opening |
| 30 | proximal surface |
| 31 | distal surface |
| 32 | flat surface |
| 33 | flat surface |
| 34 | flat surface |
| 35 | flat surface |
| 36 | angled opening |
| 37 | angled opening |
| 38 | angle |
| 39 | saw |
| 40 | gap |
| 41 | arrow |
| 42 | arrow |
| 43 | axis |
| 44 | axis |

Because many varying and different embodiments may be made within the scope of the inventive concept herein taught, and because many modifications may be made in the embodiments herein detailed in accordance with the descriptive requirement of the law, it is to be understood that the details herein are to be interpreted as illustrative and not in a limiting sense.

What is claimed as invention is:

1. A surgical instrument for enabling a surgeon to shape a patient's bone tissue with a cutting blade at a joint for receiving an implant:
    a) a cutting block body that is sized and shaped to fit a patient's bone at the joint during joint replacement surgery, the block being attachable to the patient's bone tissue at the joint area;
    b) a flat cutting guide surface on the block body for guiding a surgeon s cutting blade when the surgeon cuts bone tissue at the joint;
    c) a saw capture that removably attaches to the block body at or near the flat cutting guide surface, said saw capture having a flat guide surface thereon that is generally parallel to the cutting guide surface of the block body during use; and
    d) wherein cooperating pins and pin openings on the block body and saw capture that are angled relative to one another define a wedge locking connection for affixing the saw capture to the block body at the flat cutting guide surface, said connection including first and second interlocking connecting portions that are respectively on the block body and the saw capture, wherein the pin openings have axes that form acute angles with the axes of the pin connecting thereto.

2. The surgical instrument of claim 1 wherein the cutting block body includes flat surfaces for preparing a patient's distal femur to receive anterior and posterior cuts.

3. The surgical instrument of claim 1 wherein the cutting block body includes a plurality of flat cutting guide surfaces thereon, including at least flat cutting guide surfaces that enable a surgeon to make anterior and posterior cuts on a patient's bone and diagonally extending cutting guide surfaces that enable a surgeon to make anterior and posterior chamfer cuts on a patient's bone.

4. The surgical instrument of claim 1 wherein a gap is provided in between the saw capture flat cutting guide surface and the flat cutting guide surface of the block body, the gap being sized and shaped to allow a surgeon's saw to fit through the slot so that the saw capture and cutting block body guide the saw during cutting of the patient's bone tissue.

5. The surgical instrument of claim 1 wherein the wedge locking connection includes connection members on the end portions of the saw capture that form a connection with cooperating connecting portions on the block body so that a gap can be formed in between the saw capture and the block body and in between the connecting portions.

6. The surgical instrument of claim 1 wherein the wedge locking connection includes spaced apart sockets on the block body and cooperating pins on the saw capture that fit the sockets, and further comprising spaced apart engagement surfaces on the saw capture that engage the block body upon assembly wherein the engagements are forced tightly against the block body upon assembly.

7. The surgical instrument of claim 1 wherein the wedge locking connection includes cooperating sockets and pins.

8. The surgical instrument of claim 7 wherein the wedge locking connection includes cooperating sockets and pins respectively on the block body and saw capture, said sockets being angled with respect to the flat cutting guide surfaces.

9. The surgical instrument of claim 7 wherein the wedge locking connection includes cooperating sockets and pins, the pins extending from the flat cutting guide surface of the saw capture and the sockets being on the cutting block body.

10. The surgical instrument of claim 1 wherein the pins each have a lower end and each pin has a pair or spaced apart bearing surfaces each respectively positioned next to a pin, each bearing surface having a portion that extends beyond the lower end of a pin.

11. A surgical instrument for shaping a patient's bone tissue at the knee joint to receive an implant:
    a) a composite cutting block assembly that comprised of a plurality of connectable block elements that can be assembled together during knee joint replacement surgery, the block assembly being sized and shaped to fit a patients long bone at the knee joint during knee joint replacement surgery;
    b) a plurality of flat cutting guide surfaces on the block body for guiding a surgeon's saw blade when the surgeon cuts bone tissue at the knee joint;
    c) one of the block elements being a saw capture that removably attaches to the block assembly at or near at least one of the flat cutting guide surfaces, said saw capture having a flat guide surface thereon that is positioned generally parallel to and spaced from one of the flat cutting guide surfaces of the block assembly during use so that a gap in between the assembly and saw capture guides the surgeon's saw blade;

d) wherein interconnecting pine and pin openings on the block body and saw capture define a wedge locking connection for affixing the saw capture to the block body at the flat cutting guide surface, said connection including first and second interlocking connecting portions that are respectively on the block assembly and the saw capture wherein the pin openings have axes that form acute angles with the axes of the pins connecting thereto; and e) wherein the saw capture is gradually wedged against the block body assembly during a connection of the block assembly and saw capture so that the flat cutting guide surface of the saw capture and the flat cutting guide surface of the block assembly gradually approach one another upon such assembly.

12. The surgical instrument of claim 11 wherein the wedge locking connection includes connecting portions at the ends of the saw capture and corresponding connecting portions on the cutting block assembly, the corresponding connecting portions of the block assembly and the saw capture being sliding connections that gradually tighten the saw capture against the cutting block assembly during an affixation of the saw capture to the cutting block assembly.

13. The surgical instrument of claim 11 wherein the saw capture includes end portions having engagement that contact the cutting block assembly during use and wherein a gap is formed in between the saw capture and composite cutting block of general uniform thickness through which a surgeon's saw blade can pass during a surgical cutting of the patient's bone tissue.

14. The surgical instrument of claim 11 wherein the wedge locking connection includes pins mounted on the saw capture at the end portions thereof and sockets on the cutting block assembly that are receptive of the pins, and wherein as the pins extend deeper into the sockets, the saw capture is wedged more tightly against the cutting block assembly.

15. The surgical instrument of claim 14 wherein the sockets form an acute angle with the adjacent flat surface of the cutting block body.

16. The surgical instrument of claim 11 wherein there are a pair of pins and a pair of sockets.

17. The surgical instrument of claim 11 wherein the pins each have a lower end and each pin has a pair of spaced apart bearing surfaces each respectively positioned next to a pin, each bearing surface having a portion that extends beyond the lower end of a pin.

18. A surgical instrument for shaping a patient's bone tissue at a joint to receive an implant:

a) a cutting block body that is sized and shaped to fit a patient's long bone at the joint during joint replacement surgery, the block being attachable to the patient's bone tissue at the joint area;

b) a flat cutting guide surface on the block body for guiding a surgeon's saw blade when the surgeon cuts bone tissue at the joint;

c) a saw capture that removably attaches to the block body at or near the flat cutting guide surface, said saw capture having a flat guide surface thereon that is generally parallel to the cutting guide surface of the block body during use;

d) wherein cooperating removably connectable projections and openings on the block body and saw capture define a wedge locking connection for affixing the saw capture to the block body at the flat cutting guide surface, said connection including first and second interlocking connecting portions that are respectively on the block body and the saw capture, wherein the openings have axes that form acute angles with the projection connecting thereto; and e) wherein the saw capture is gradually wedged against the block body upon assembly of the block body and saw capture so that the flat cutting guide surface of the saw capture and the flat cutting guide surface of the block body gradually approach one another upon such assembly until a Wedge lock or interference fit is achieved.

* * * * *